United States Patent [19]
Kronekvist

[11] Patent Number: 5,921,235
[45] Date of Patent: Jul. 13, 1999

[54] VAPORIZER CAROUSEL

[75] Inventor: Hans Kronekvist, Stockholm, Sweden

[73] Assignee: Siemens Elema AB, Solna, Sweden

[21] Appl. No.: 09/025,476

[22] Filed: Feb. 18, 1998

[30] Foreign Application Priority Data

Feb. 20, 1997 [SE] Sweden ................................. 9700595

[51] Int. Cl.⁶ .................................................. A61M 16/00
[52] U.S. Cl. ................................ 128/203.12; 128/203.28; 222/144
[58] Field of Search ................ 128/203.12, 203.28, 128/204.28, 205.13, 205.15, 200.14, 200.19; 222/144, 325; 137/614.04, 599.1

[56] References Cited

U.S. PATENT DOCUMENTS

| | | |
|---|---|---|
| 4,058,120 | 11/1977 | Caparrelli et al. . |
| 4,253,453 | 3/1981 | Hay . |
| 4,434,790 | 3/1984 | Olesen ................................. 128/200.14 |
| 5,807,316 | 9/1998 | Teeple, Jr. ................................. 604/51 |

FOREIGN PATENT DOCUMENTS

| 0 376 649 | 4/1990 | European Pat. Off. . |
|---|---|---|
| 255 258 | 11/1911 | Germany . |

*Primary Examiner*—John G. Weiss
*Assistant Examiner*—Charles W. Anderson
*Attorney, Agent, or Firm*—Hill & Simpson

[57] ABSTRACT

A vaporizer carousel for an anaesthetic machine has a gas supply device on which a holder for at least one vaporizer is arranged in a rotating fashion. A coaxial gas coupling area is arranged between the gas supply device and the holder in order to achieve an uninterrupted flow of gas between the gas supply device and the holder, regardless of the holder angle of rotation in relation to the gas supply device. The coaxial gas coupling area is formed by first and second connecting conduit in the gas supply device, first and second gas conduits in the holder and a gas space between the gas supply device and the holder.

10 Claims, 4 Drawing Sheets

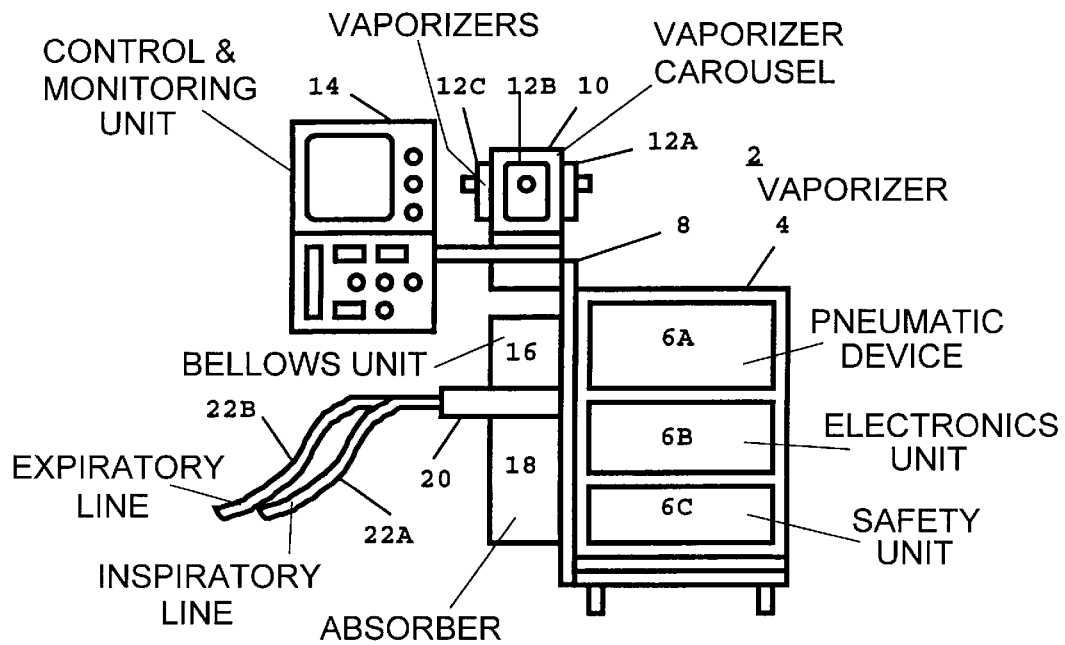
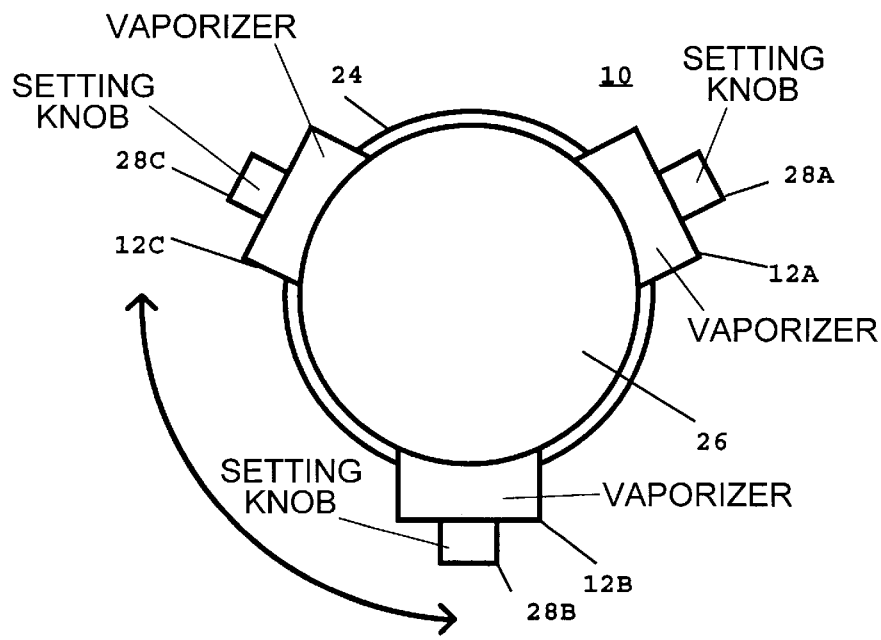
FIG. 1
FIG. 2

VAPORIZER CAROUSEL

BACKGROUND OF THE INVENTION

1. Field of the Invention

The present invention is directed to a vaporizer carousel for an anaesthetic apparatus of the type having a holder for at least one vaporizer, a gas conduit system in the holder, and a gas supplied device which the holder is rotatably arranged, with the gas supply device having respective connections for carrying gas to and from the gas conduit system.

2. Description of the Prior Art

A vaporizer carousel with a rotating holder for three vaporizers is described in U.S. Pat. No. 4,058,120. Each vaporizer is equipped with one gas inlet and one gas outlet (i.e. a separate pair of connectors for each vaporizer). The holder is placed on a gas manifold provided with one gas inlet and one gas outlet. The inlet and the outlet are arranged so they can be connected in turn to a respective pair of vaporizer connectors when the holder is rotated. Only one vaporizer at a time can therefore be connected to the gas manifold's gas inlet and gas outlet to deliver anaesthetic to a gas flowing through the vaporizer. For each connection position for the holder, i.e. relative to each vaporizer's pair of connectors, the position of the holder is fixed in relation to the gas manifold by a lock.

An inhalation apparatus with four bottles for liquids rotationally arranged on a hollow rod is described in German Patentschrift 255,258. Radial gas channels are arranged in the rod so a gas can be delivered to one bottle at a time. The bottle to receive gas is rotated to a position at which it connects to the radial gas channels. Bottles are locked in this position by a spring-loaded pin.

With these devices, gas flow must be turned off whenever a new vaporizer or bottle is to be connected, the rotating part must be unlocked and turned to a new exact position for the vaporizer or bottle to be connected, the new vaporizer or bottle must be locked in the new position and the gas flow must be turned back on. With vaporizer carousels, this means that residual anaesthetic gas in gas conduits could escape into the operating room when a vaporizer or bottle is disconnected. The mixing of two anaesthetic agents when a new vaporizer is activated also poses a major risk, since some "old" anaesthetic gas always remains in conduits leading from the vaporizer carousel. This situation should be avoided completely, since the effect of such anaesthetic mixing on the patient is unknown.

Moreover, the vaporizer carousel/inhalation apparatus cannot be rotated once a vaporizer/liquid bottle has been activated. This restricts the operator's freedom of movement when using the system. In modern operating rooms employing a large amount of technical equipment connected to the patient, space near the patient can be very cramped during surgery in certain situations. It would therefore be advantageous if e.g. the anaesthesiologist was not forced to sit at a particular location the entire time in order to exercise control over the patient and the anaesthesia machine, but be able to move about more freely around the anaesthesia equipment and patient, with no loss of control.

SUMMARY OF THE INVENTION

An object of the present invention is to provide a vaporizer carousel which solves the aforementioned problems.

The above object is achieved in accordance with the principles of the present invention in a vaporizer carousel of the type initially described wherein the gas conduit system of the holder, and/or at least one of the gas connections, forms a coaxial gas coupling area between the gas supply device and the holder, allowing gas to be carried to or from the holder, regardless of the angle of rotation of the holder relative to the gas supply device.

By utilizing a coaxial gas coupling area between the holder and the gas supply device, the holder's angle of rotation With respect to the gas supply device does not matter, since gas connections between the holder and the gas supply device are open and intact at all times. The vaporizer carousel therefore can be freely rotated in any direction, regardless of whether a vaporizer has been activated. It is then very easy for an anaesthetist to change position in relation to the patient while retaining full control over which vaporizer is activated and which concentration is set on the active vaporizer. If necessary, the anaesthetist, despite changing position, can still change the concentration of the anaesthetic by rotating the holder until the activated vaporizer reaches a position at which the concentration can conveniently be re-set.

When switching to another vaporizer, the anaesthetist turns off the active vaporizer and rotates the vaporizer carousel to gain access to the vaporizer to be activated. Meanwhile, gas continues to flow through the vaporizer carousel's gas conduit system (without carrying any anaesthetic gas), thereby flushing out any of the first anaesthetic gas still remaining in the system. When the anaesthetist subsequently activates the new vaporizer containing another anaesthetic, there is therefore no risk of anaesthetics being mixed after the vaporizer carousel.

Simultaneous activation of two or more vaporizers (when the vaporizer carousel is equipped with a number of vaporizers) is appropriately prevented with some form of interlock system which can be electronic, mechanical or a combination thereof. The aforementioned known vaporizer carousels do not have any interlock systems, since only one vaporizer at a time can be connected to the gas flow. Interlock systems are frequently incorporated into the more common vaporizer devices in which a number of vaporizers are arranged in a row.

DESCRIPTION OF THE DRAWINGS

FIG. 1 is a schematic illustration of an anaesthetic machine with a vaporizer carousel according to the invention.

FIG. 2, as used in the anaesthetic machine of FIG. 1, shows a vaporizer carousel in an overhead view.

DESCRIPTION OF THE PREFERRED EMBODIMENTS

Figure 3:
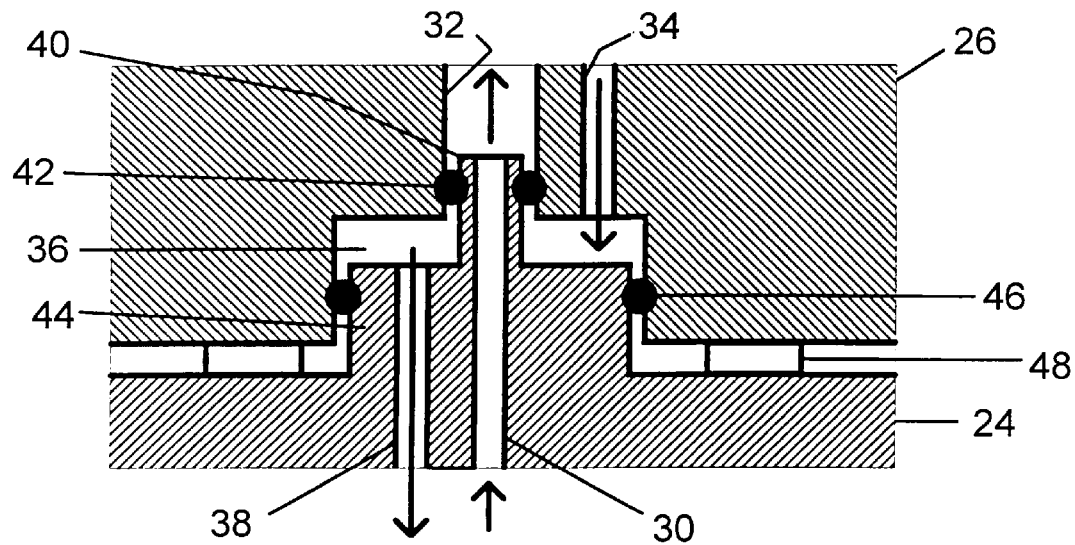
FIG. 3 shows a first embodiment of a coaxial gas coupling area in the vaporizer carousel according to the invention.

FIG. 1 shows an anaesthetic apparatus 2, including a cart 4 with a pneumatic device 6A for gas regulation equipment, an electronics unit 6B for electronic control equipment and a 20 safety unit 6C with a battery for use in the event of a power failure. A stand 8, containing gas and signal conduits, is mounted on the cart 4. A vaporizer carousel 10 is arranged on the stand 8. The vaporizer carousel 10 is equipped with a first vaporizer 12A, a second vaporizer 12B and a third vaporizer 12C, which can hold the same or different anaesthetics.

A rotating control and monitoring unit 14 is arranged on the stand 8, and a bellows unit 16 and an absorber 18 are connected to a patient cassette 20 on the stand 8. An inspiratory line 22A and an expiratory line 22B, intended for connection to the patient by a Y-piece or the equivalent, run from the patient cassette to the patient who is to be anaesthesized.

As FIG. 2 shows, the vaporizer carousel 10 has a gas supply device 24 and a holder 26. The holder 26 (holding the vaporizers 12A, 12B, 12C) can be rotated freely in relation to the gas supply device 24. The vaporizers 12A, 12B, 12C can be seated in appropriately shaped recesses in the holder 26 (not shown in the figure). The holder 26 of the vaporizer carousel 10 can be devised for a larger or smaller number of vaporizers 12A, 12B, 12C than the three shown in the figure. Utilization of all the recesses in the holder 26 is not necessary during equipment operation. In functional respects, having one vaporizer 12A (or either of 12B, 12C) in the holder 26 is sufficient.

Each vaporizer 12A, 12B, 12C is equipped with a setting knob 28A, 28B, 28C for activating one of the vaporizers 12A, 12B, 12C and setting the desired concentration of anaesthetic gas to be delivered thereby.

As noted above, the holder 24 can be freely rotated in relation to the gas supply device 24. This is achieved by a coaxial gas coupling area, arranged between the holder 26 and the gas supply device 24. A first embodiment of the coaxial gas coupling area between the gas supply device 24 and the holder 26 in the vaporizer carousel 10 is shown in FIG. 3.

Gas, which can be in the form of a pure gas (e.g. oxygen) or a gas mixture (e.g. a mixture of oxygen and nitrous oxide) prepared in the pneumatic unit 6A in the anaesthetic machine 2 (FIG. 1), is carried in a gas conduit (not shown) in the stand 8 to a first gas connector 30 in the gas supply device 24 and from there to a first gas conduit 32 in the holder 26 for subsequent delivery to the vaporizers 12A, 12B, 12C according to the description below. After passing the vaporizers 12A, 12B, 12C, gas, possibly containing an anaesthetic, then flows through a second gas conduit 34 in the holder 26 down to a gas space 36 and out through a second gas connector 38 in the gas supply device 24.

The first gas connector 30 is located in a first shoulder 40 which is arranged in a gas-tight fashion in the first gas conduit in center of rotation of the holder 26 and the gas supply device 24. A sealing gasket 24, e.g. an O-ring, keeps gas from leaking into the gas space. The gas space 36 is a space between the holder 24 and a second shoulder 44 in the gas supply device 24. The second shoulder 44 is also arranged in a gas-tight fashion with a sealing gasket 46 in the holder To facilitate rotation of the holder 26, the holder is appropriately arranged on the gas supply device 24 with some form of bearing 48. Since the gas space 36 totally surrounds the first shoulder 40 and is also in constant gas connection with both the second conduit 34 and the second gas connector 38, gas is able to pass continuously from the gas supply device 24 through the first gas connector 30 to and from the holder 26, via the second gas conduit 34, the gas space 36 and the second gas connector 38 in the gas supply device 24. It does not matter how the holder 26 is rotated in relation to the gas supply device 24, since the gas space 36 ensures that there is a constant gas connection between the second gas conduit 34 and the second gas connector 38.

Naturally, the holder 26 can instead be devised with two shoulders arranged in a cavity in the gas supply device 24 to form the coaxial gas coupling area.

Figure 4:
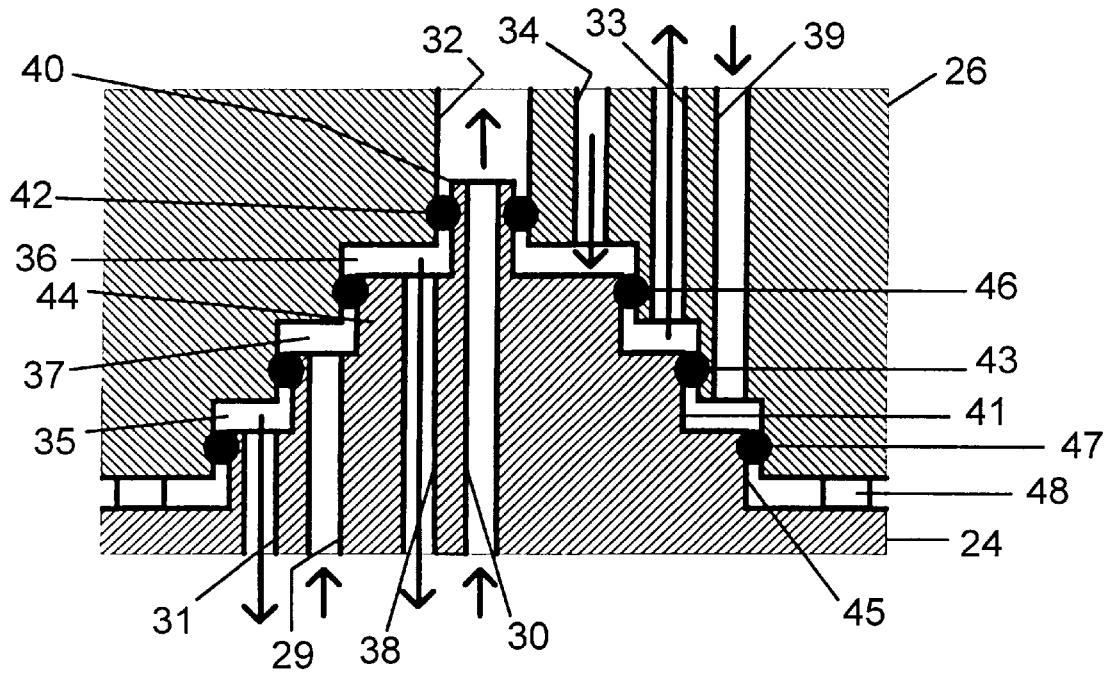
FIG. 4 shows a second embodiment of a coaxial gas coupling area in the vaporizer carousel according to the invention.

FIG. 4 shows a second embodiment of the coaxial gas coupling area. Items identical to items in the first embodiment have been assigned the same reference designations. In principle, the second embodiment is a generalization of the first embodiment which allows more coaxial gas couplings to be made. Thus, FIG. 4 shows a third shoulder 41 with the seal 43. The third shoulder 41 forms a second gas space 37 to which a third gas connector 29 and a third gas conduit 33 are connected in order to supply the holder 24 with gas. In a like manner, a fourth shoulder 45 is arranged with a seal 47 to form a third gas space 35. A fourth gas connector 31 and a fourth gas conduit 39 are connected to the third gas space in order to carry gas from the holder 24 to the gas supply device 26.

In principle, the multiple coaxial gas coupling area can have an arbitrary number of gas connectors and gas conduits and can be used for directing gas in different ways. Instead of paired delivery and removal of gas, all gas can be supplied to the holder 24 through one conduit and removed through one or more of the other conduits in the coaxial gas coupling area.

It should be noted that the gas connectors 29, 31, 38 and the gas conduits 33, 34, 39 can be deployed in an optional fashion in relationship to each other, i.e. along the same radial line on the gas supply device 24 and holder 26 respectively, or along radial lines with differing angles between them. The latter option can be employed in order to achieve as compact a design as possible.

Figure 5:
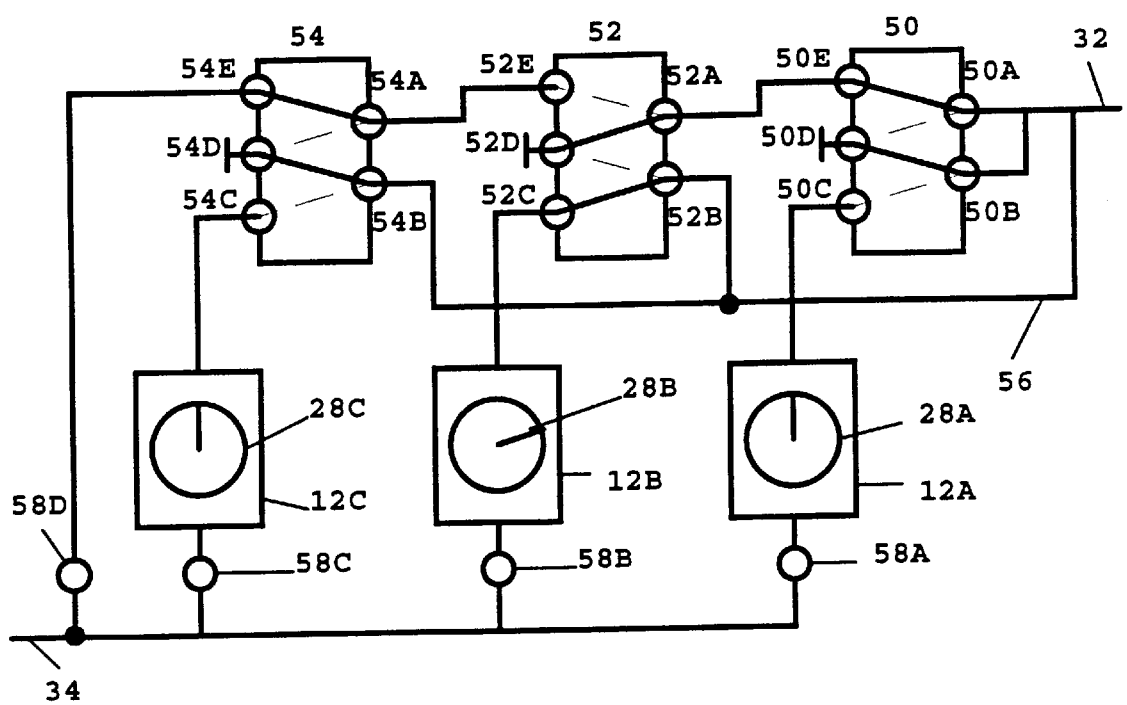
FIG. 5 shows a gas conduit system in the vaporizer carousel according to the invention.

FIG. 5 shows the way the gas conduit system in the holder can be devised to carry gas to any of the vaporizers 12A, 12B, 12C or to bypass all the vaporizers 12A, 12B, 12C. The first gas conduit 32 carries gas from the gas supply device 24 to a first valve 50, devised with two valve inlets 50A, 50B and three valve outlets 50C, 50D, 50E, the second valve outlet 50D being blocked. The two gas inlets 50A, 50B to the first valve 50 are interconnected. The first valve outlet 50C on the first valve 50 is connected to the first vaporizer 12A, and the third valve outlet 50E on the first valve 50 is connected to a second valve 52. The second valve 52 is also devised with two valve inlets 52A, 52B and three valve outlets 52C, 52D, 52E, the second valve outlet 52D being blocked.

The first valve inlet 52A on the second valve 52 is connected to the third valve outlet 50E on the first valve 50. The second valve inlet 52B on the second valve 52 is directly connected to the first gas conduit 32 by means of the gas connector 56. The first valve outlet 52C on the second valve 52 is connected to the second vaporizer 12B, and the third valve outlet 52E on the second valve 52 is connected to a third valve 54. The third valve 54 is also devised with two valve inlets 54A, 54B and three valve outlets 54C, 54D, 54E, the second valve outlet 54D being blocked.

The first valve inlet 54A on the third valve 54 is connected to the third valve outlet 52E on the second valve 52. The second valve inlet 54B on the third valve 54 is connected to the first gas conduit 32 via the gas connector 56. The first valve outlet 54C on the third valve 54 is connected to the third vaporizer 12C, and the third valve outlet 54E on the third gas valve 54 is connected to the second gas conduit 34.

All the vaporizers 12A, 12B, 12C are connected to the second gas conduit 34 on the outlet side. Check valves 58A, 58B, 58C, 58D are arranged in the gas conduit system to prevent gas from flowing through a conduit in the wrong direction.

In principle, the valves 50, 52, 54 have two positions and are able to assume an activated or a neutral position. In the neutral position, the first valve inlet 50A, 52A, 54A is connected to the third valve outlet 50E, 52E, 54E, and the second valve inlet 50B, 52B, 54B is connected to the second valve outlet 50D, 52D, 54D. In the activated position, the first valve inlet 50A, 52A, 54A is connected to the second value outlet 50D, 52D, 54D, and the second valve inlet 50B, 52B, 54B is connected to the first valve outlet 50C, 52C, 54C.

The valves 50, 52, 54 are devised to prevent interruption in the flow of gas through the holder 24 when any of the valves 50, 52, 54 is switched. Instead, flow gradually increases through the valve outlet to which switching is made, whereas flow gradually declines through the valve outlet from which switching was made. This accordingly prevents any interruption in the flow of gas.

All the gas from the gas supply device 32 therefore will flow in through the first gas conduit 32 and pass through the valves 50, 52, 54 and the fourth check valve 58D straight to the second gas conduit 34 when none of the valves 50, 52, 54 is activated (neutral position for all the valves 50, 52, 54). In order to describe events occurring when a vaporizer 12A, 12B, 12C is activated, FIG. 5 shows how the second vaporizer 12B has been activated with the second setting knob 28B. The second valve 52 has been switched from the neutral to the active position. Switching can be performed either electronically or by means of some mechanical linkage between the second setting knob 28B and the second valve 52. Gas will then flow from the first gas conduit 32, through the gas connector 56, to the second valve inlet 52B on the second valve and on, through the first valve outlet 52C on the second valve 52, to the second vaporizer 12B. The set amount of anaesthetic is vaporized in the second vaporizer 12B and carried, via the second check valve 58B, to the second gas conduit 34. When the second vaporizer 12B is activated, it is also automatically locked in position in the vaporizer carousel 10 to keep it from being detached by mistake while gas is flowing through it.

With the gas conduit system shown in FIG. 5, the first vaporizer 12A, for example, can be removed from the vaporizer carousel 10 without any risk of gas leakage, even if one of the other vaporizers 12B, 12C is activated. The first check valve 58A effectively keeps gas from flowing in the wrong direction, to the empty position, and the first valve 50 cannot be activated, since the activating link between the first setting knob 28A and the first valve 50 is broken when the first vaporizer 12A is removed.

An interlock system is arranged in the holder 26 to keep more 10 than one vaporizer 12A, 12B, 12C from being activated at the same time. The interlock system can be electrical or mechanical and is not described in more detail in this application.

Figure 6:
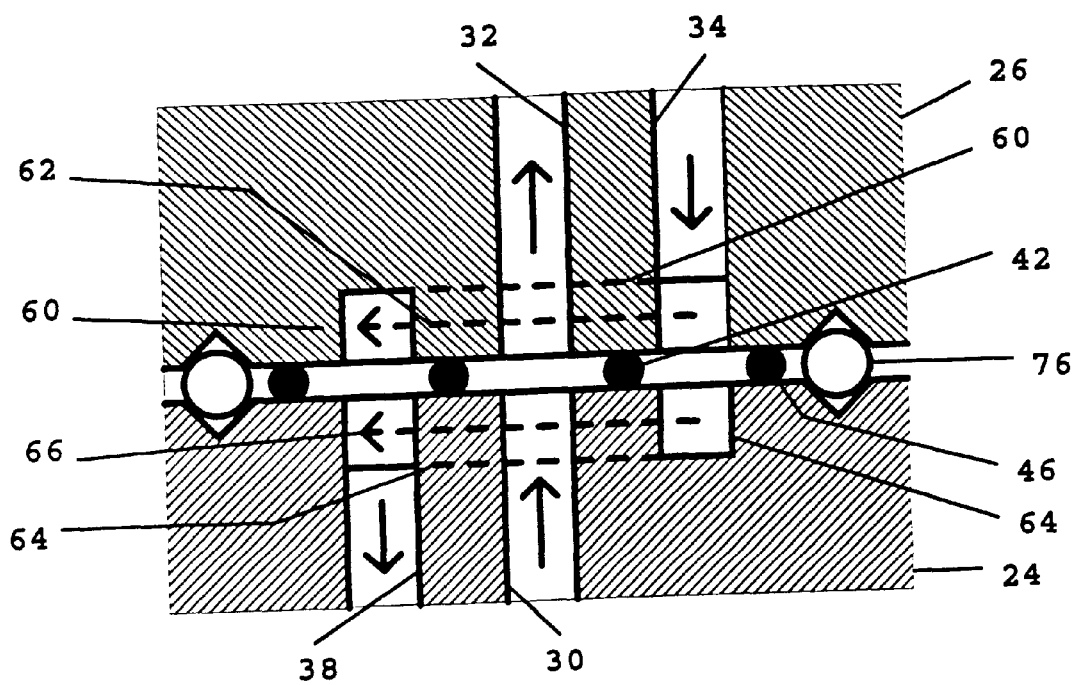
FIG. 6 shows a third embodiment of a coaxial gas coupling area in the vaporizer carousel according to the invention.

FIG. 6 shows a third embodiment of the coaxial gas coupling 15 area between the gas supply device 24 and the holder 26. Items which can be identical to those in the preceding embodiment have the same designations.

The first gas conduit 32 is arranged at the holder 26 center of rotation. A first concentric gas channel 60 is arranged in the holder 26 and encircles the first gas conduit 32. The first concentric gas channel 60 is connected to the second gas conduit 34. Gas from the second gas conduit 34 can flow unimpeded through the first concentric gas channel 60, as designated by the dashed arrow 62, i.e. around the first gas conduit 32. The cross-sectional area of the first concentric gas channel 60 is at least as large as the cross-sectional area of the second gas conduit 34 to keep resistance to flow from becoming unnecessarily large.

In the corresponding manner, a second concentric gas channel 64 can be arranged in the gas supply device 24, either instead of or in combination with the first concentric gas channel 60. The second concentric gas channel 64 is connected to the second gas connector 38. Gas can flow unimpeded around the first gas connector 30 in the second concentric gas channel 64, as shown by the arrow 66.

Since the two concentric gas channels 60 and 64 lie along the 5 same radius from the center of rotation, they form, with the first gas connector 30 and the first gas conduit 32, a coaxial gas coupling area in which the holder 26 can be rotated to any angle in relation to the gas supply unit 24 without interruption to the flow of gas.

When two concentric gas channels 60 and 64 are utilized, their total cross-sectional area must be adapted to other paths of flow.

If only one concentric gas channel 60 and 64 is utilized, e.g. the first concentric gas channel 60 in the holder 26, the same effect is achieved when the second gas connector 38 lies at the same distance from the center of rotation as the first concentric gas channel 60.

The holder 26 and the gas supply unit 24 are kept from sliding apart radially by the use of an appropriate bearing, illustrated with the bearing 76 in FIG. 6, or some corresponding device. Sealing gaskets 42, 46 are arranged on contact surfaces between the holder 26 and gas supply device 24.

Figure 7:
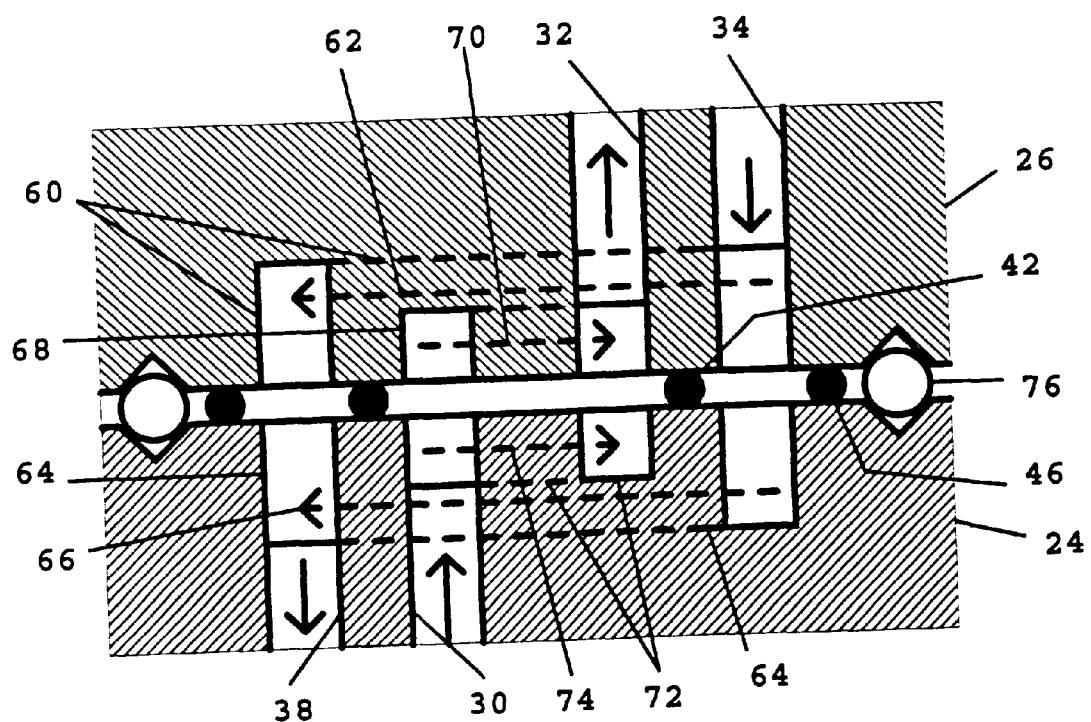
FIG. 7 shows a fourth embodiment of a coaxial gas coupling 15 area in the vaporizer carousel according to the invention.

FIG. 7 shows a fourth embodiment of the coaxial gas coupling area. As in previous embodiments, all identical items have retained their designations. In principle, the difference compared to FIG. 5 is that a third concentric gas channel 68 has been arranged inside the first concentric gas channel 60, and the first gas channel 32 is placed at a distance corresponding to the radius of the third concentric gas channel 68 from the center of rotation of the holder 26. Gas can thereby flow unimpeded through the third concentric gas channel 68, as shown by the dashed arrow 70. In a corresponding manner, a fourth concentric gas channel 72, through which gas can flow unimpeded according to the dashed arrow 74, is arranged in the gas supply unit 24.

Otherwise, the description of the second embodiment also applies to the third embodiment.

Additional concentric gas channels with their respective gas connectors and gas conduits can be arranged in the gas coupling area according to FIG. 7 (analogous to the embodiment in FIG. 4).

Combinations of the described embodiments can be made where appropriate. For example, the embodiment according to FIG. 6 can be combined with the embodiment according to FIG. 3 when the gas supply device 24 is equipped with a shoulder which is coupled in a non-leaking fashion to the first gas conduit 32 in the same way as for the first shoulder 40 in FIG. 3. As noted above, it does not matter whether one or a number of concentric gas channels is/are used in the holder 26 or gas supply device 24. Of primary significance is that a coaxial gas coupling area is achieved in which gas can be carried between the gas supply device 24 and the holder 26, regardless of the angle of rotation of the holder 26 in relation to the gas supply device 24.

Although various minor modifications might be suggested by those skilled in the art, it should be understood that I wish to embody within the scope of the patent warranted hereon all such modifications as reasonably and properly come with the scope of my contribution to the art.

I claim as my invention:

1. A vaporizer carousel for an anaesthetic apparatus, said vaporizer carousel comprising:

a gas supply device having at least one first gas connector and a second gas connector;

a holder rotatably mounted relative to said gas supply device, said holder being rotatable through a plurality of rotational angles relative to said gas supply device;

a gas conduit system in said holder connectible to said at least one first gas connector and to said second gas connector for exchanging gas between said gas conduit system and said gas supply device; and at least one of said gas conduit system and said first gas connector and said second gas connector forming a co-axial gas coupling area between said gas supply device and said holder for allowing gas exchange between said holder and said gas supply device independently of the rotational angle of said holder.

2. A vaporizer carousel as claimed in claim 1 wherein said gas supply device comprises at least two contiguous shoulders which form a gas-tight space with said holder comprising said coaxial gas coupling area, and wherein said first gas connector is disposed in a first of said shoulders and is connected to a first gas conduit in said gas conduit system, and wherein said second gas connector is disposed in a second of said shoulders and is connected to said gas-tight space, and wherein said gas conduit system includes a second gas conduit connected to said gas-tight space.

3. A vaporizer carousel as claimed in claim 2 wherein said gas supply device comprises a third shoulder which forms a second gas-tight space with said holder and a third shoulder which forms a third gas-tight space between said third and fourth shoulders and said holder, said carousel comprising a third gas connector disposed in said third shoulder and connected to said second gas-tight space, a third gas conduit in said gas conduit system connected to said second gas-tight space, a fourth gas connector disposed in said fourth shoulder and connected to said gas-tight space, and a fourth gas conduit in said gas conduit system connected to said third gas-tight space.

4. A vaporizer carousel as claimed in claim 1 wherein said gas conduit system includes first and second gas conduit and wherein at least one of said holder and said gas supply device comprise a gas channel concentrically surrounding said first gas conduit and forming said coaxial gas coupling area, said second gas conduit and said second gas connector being connected to said gas channel.

5. A vaporizer carousel as claimed in claim 4 wherein at least one of said holder and said gas supply device comprises a further gas channel inside and concentric with said gas channel, and wherein said first gas connector and said first gas conduit are connected to said further gas channel.

6. A vaporizer as claimed in claim 4 wherein at least one of said holder and said gas supply device comprise a plurality of further gas channels concentric with said gas channel and a plurality of further gas connectors and further gas conduits in said gas conduit system, said further gas connectors and said further gas conduits being respectively connected to said further concentric gas channels.

7. A vaporizer carousel as claimed in claim 1 wherein at least one of said holder and said gas supply device comprises a gas channel concentrically surrounding said first gas connector and forming said coaxial gas coupling area, said gas conduit system having a gas conduit connected to said gas channel and said second gas connector also being connected to said gas channel.

8. A vaporizer carousel as claimed in claim 7 wherein at least one of said holder and said gas supply device comprises a further gas channel inside and concentric with said gas channel, and wherein said first gas connector and said gas conduit are connected to said further gas channel.

9. A vaporizer as claimed in claim 7 wherein at least one of said holder and said gas supply device comprise a plurality of further gas channels concentric with said gas channel and a plurality of further gas connectors and further gas conduits in said gas conduit system, said further gas connectors and said further gas conduits being respectively connected to said further concentric gas channels.

10. A vaporizer carousel as claimed in claim 1 wherein said gas conduit system includes a valve system having a non-activated state and an activated state, said valve system in said non-activated state carrying all gas from said first gas connector directly to said second gas connector and in said activated state, carrying gas to a gas inlet of an activated vaporizer on said vaporizer carousel.

\* \* \* \* \*